United States Patent
Inoue et al.

(10) Patent No.: US 9,616,046 B2
(45) Date of Patent: Apr. 11, 2017

(54) HEPATOCYTE-PROLIFERATING AGENT

(71) Applicant: JAPAN BIO PRODUCTS CO., LTD., Shibuya-ku, Tokyo (JP)

(72) Inventors: Shinjiro Inoue, Tokyo (JP); Eiichi Hirano, Tokyo (JP); Tetsuo Morinaga, Tokyo (JP)

(73) Assignee: JAPAN BIO PRODUCTS Co., Ltd., Shibuya-Ku (JP)

( * ) Notice: Subject to any disclaimer, the term of this patent is extended or adjusted under 35 U.S.C. 154(b) by 0 days.

(21) Appl. No.: 14/900,222

(22) PCT Filed: Jun. 16, 2014

(86) PCT No.: PCT/JP2014/065879
§ 371 (c)(1),
(2) Date: Dec. 21, 2015

(87) PCT Pub. No.: WO2014/208381
PCT Pub. Date: Dec. 31, 2014

(65) Prior Publication Data
US 2016/0151330 A1     Jun. 2, 2016

(30) Foreign Application Priority Data

Jun. 28, 2013 (JP) ................. 2013-136178

(51) Int. Cl.
*A61K 31/4015* (2006.01)
*A61K 31/198* (2006.01)
*C12N 5/071* (2010.01)

(52) U.S. Cl.
CPC ........ *A61K 31/4015* (2013.01); *A61K 31/198* (2013.01); *C12N 5/067* (2013.01); *C12N 2500/32* (2013.01); *C12N 2500/33* (2013.01); *C12N 2501/999* (2013.01)

(58) Field of Classification Search
CPC ................................ A61K 31/4015
USPC ........................................ 514/423
See application file for complete search history.

(56) References Cited

FOREIGN PATENT DOCUMENTS

| JP | H11-322612 A | 11/1999 |
|---|---|---|
| JP | 2002000263 A | 1/2002 |
| JP | 2002-520013 A | 7/2002 |
| JP | 2003-113095 A | 4/2003 |
| JP | 2008-201749 A | 9/2008 |
| WO | 00/02999 A2 | 1/2000 |
| WO | 2012/030217 A2 | 3/2012 |
| WO | 2014/077289 A1 | 5/2014 |

OTHER PUBLICATIONS

SciLab.com: Material and Safety Data Sheet (MSDS), (2005), pp. 1-5.*
The Univ. of Arizona: The Biol. Project Biochem. (2003), pp. 1-2.*
Li, C-Y et al., "Recombinant human hepassocin stimulates proliferation of hepatocytes in vivo and improves survival in rats with fulminant hepatic failure," Gut. 2010; 59(6):817-26.
International Preliminary Report on Patentability, issued in International Application No. PCT/JP2014/065879, mailed on Jan. 7, 2016.
Liu Ke-Xin et al., "Kan Saisei ni Oyobosu Laennec no Eikyo (Effect of Laennec on Liver Regeneration)," Clinical Pharmacology and Therapy, vol. 5, No. 12, pp. 2187-2194. (English abstract) (Cited in IPRP).
Yang et al., "Protective effect of JBP485 on concanavalin A-induced liver injury in mice," Journal of Pharmacy and Pharmacology, vol. 61, 2009, pp. 767-774. (Cited in IPRP).

* cited by examiner

*Primary Examiner* — Taofiq A Solola
(74) *Attorney, Agent, or Firm* — Andrews Kurth Kenyon LLP

(57) ABSTRACT

The present invention relates to a hepatocyte-proliferating agent comprising pyroglutamic acid, aspartic acid, and glutamic acid as active ingredients, in particular, a hepatocyte-proliferating agent capable of selectively proliferating normal hepatocytes without proliferating cancer cells.

12 Claims, 2 Drawing Sheets

HEPATOCYTE-PROLIFERATING AGENT

CROSS-REFERENCE TO RELATED APPLICATIONS

This is a national phase application based on the PCT International Patent Application No. PCT/JP2014/065879 filed Jun. 16, 2014, claiming priority to Japanese Patent Application No. 2013-136178 filed Jun. 28, 2013, the entire contents of both of which are incorporated herein by reference.

TECHNICAL FIELD

The present invention relates to a hepatocyte-proliferating agent.

BACKGROUND ART

The liver is an organ assuming an important role, for example, in metabolism, excretion, detoxification, and the maintenance of body fluid homeostasis. The liver is known to recover its function and morphology in a short period when it is partially excised since the liver has a high regenerative ability.

CITATION LIST

Patent Literature

Patent Literature 1: Japanese Unexamined Patent Publication No. 2003-113095
Patent Literature 2: Japanese Unexamined Patent Publication No. H11-322612
Patent Literature 3: Japanese Unexamined Patent Publication No. 2008-201749

Non Patent Literature

Non Patent Literature 1: Recombinant human hepassocin stimulates proliferation of hepatocytes in vivo and improves survival in rats with fulminant hepatic failure (Gut. 2010 June; 59(6): 817-26.)

SUMMARY OF INVENTION

Technical Problem

However, the in-vitro culture of hepatocytes tends to not sufficiently increase the number of the cells.

In the field of basic research, as a means for analyzing biotissue cells in detail, a method has been established, which involves culturing the cells removed from the biotissue to the outside of the body and further dividing and proliferating the cultured cells for successive survival. However, for human hepatocytes and rat hepatocytes, it is very difficult to proliferate primary hepatocytes isolated from mature individuals by culture.

Growth factors, such as epidermal growth factor (EGF), transforming growth factor (TGF-α), hepatocyte growth factor (HGF), and fibroblast growth factor (FGF), insulin, interleukin-6 (IL-6), tumor necrosis factor-α (TNF-α), norepinephrine, and the like are known to promote the proliferation of hepatocytes in in-vitro cell culture.

It is known that both EGF and TGF-α show proliferative activity in fibroblasts as well as epithelial cells and hepatocyte growth factor promotes the proliferation of vascular endothelial cells and fibroblasts as well as epithelial cells.

Cancer cells express increased EGF receptors compared to normal cells. Thus, when a cell population including both cancer cells and normal cells is exposed to the above-described growth factors, the proliferation of not only the normal cells but also the cancer cells is enhanced.

To date a glycoprotein with a molecular weight of 57 kilodaltons, consisting of royal jelly is known as a factor promoting the DNA synthesis of hepatocytes, i.e., promoting the proliferation of hepatocytes (Patent Literature 1).

A hepatocyte growth factor inducer containing a prostanoic acid derivative as an active ingredient (Patent Literature 2) and a hepatocyte growth factor production inducer containing a treated product of Cordyceps sinensis as an active ingredient (Patent Literature 3) are reported. The hepatocyte growth factor inducer or the hepatocyte growth factor production inducer is not an agent directly working on the proliferation of hepatocytes but an agent inducing the production and secretion of hepatocyte growth factor and indirectly promoting the proliferation of hepatocytes.

Human Hepassocin (HPS) (Non Patent Literature 1) is known as a factor proliferating hepatocytes other than the above. It is known that HPS is a protein specifically expressed on hepatocytes and significantly enhances the proliferation of hepatocytes. The gene encoding BPS has been cloned as cDNA.

Made in view of the above-described circumstances, the present invention has an object of providing a hepatocyte-proliferating agent capable of selectively proliferating normal hepatocytes without proliferating cancer cells.

Solution to Problem

As a result of intensive studies for achieving the above object, the present inventors have found that a mixture containing pyroglutamic acid, aspartic acid and glutamic acid promotes the proliferation of hepatocytes, thereby accomplishing the present invention.

The mixture has no risk of proliferating cancer cells. Plus, the mixture has proliferative activity equivalent to or higher than those of the conventional factors proliferating hepatocytes. The mixture enables the proliferation of hepatocytes in vitro and will form extremely effective means in the field of basic research, the fields of drug discovery research, bioreactors, liver disease treatment, and regenerative medicine, and the like.

Thus, the present invention provides the following [1] to [8].

[1] A hepatocyte-proliferating agent comprising pyroglutamic acid, aspartic acid, and glutamic acid as active ingredients.

[2] The hepatocyte-proliferating agent according to [1], wherein a molar ratio of each of the active ingredients is pyroglutamic acid aspartic acid:glutamic acid=5 to 200:7 to 28:1 to 16.

[3] The hepatocyte-proliferating agent according to [1] or [2], wherein the hepatocyte-proliferating agent is a solution, in which a concentration of pyroglutamic acid is 0.5 to 20 mM.

[4] The hepatocyte-proliferating agent according to any one of [1] to [3], wherein the hepatocyte-proliferating agent is a solution, in which a concentration of aspartic acid is 0.7 to 2.8 mM and a concentration of glutamic acid is 0.1 to 1.6 mM.

[5] A therapeutic agent for a liver disease, comprising the hepatocyte-proliferating agent according to any one of [1] to [4].

[6] The therapeutic agent according to [5], wherein the liver disease is liver cancer.

[7] A liver-regenerating agent, comprising the hepatocyte-proliferating agent according to any one of [1] to [4].

[8] A liver function-recovering agent, comprising the hepatocyte-proliferating agent according to any one of [1] to [4].

The present invention further provides the following [9] to [20].

[9] A method for proliferating normal hepatocytes, comprising a step of administering effective amounts of pyroglutamic acid, aspartic acid, and glutamic acid to a subject.

[10] A method for regenerating a liver, comprising a step of administering effective amounts of pyroglutamic acid, aspartic acid, and glutamic acid to a subject.

[11] A method for recovering liver function, comprising a step of administering effective amounts of pyroglutamic acid, aspartic acid, and glutamic acid to a subject.

[12] A method for treating or preventing a liver disease, comprising a step of administering effective amounts of pyroglutamic acid, aspartic acid, and glutamic acid to a subject.

[13] Pyroglutamic acid, aspartic acid, and glutamic acid for proliferating normal hepatocytes.

[14] Pyroglutamic acid, aspartic acid, and glutamic acid for regenerating a liver.

[15] Pyroglutamic acid, aspartic acid, and glutamic acid for recovering liver function.

[16] Pyroglutamic acid, aspartic acid, and glutamic acid for treating or preventing a liver disease.

[17] Use of pyroglutamic acid, aspartic acid, and glutamic acid in the manufacture of a hepatocyte-proliferating agent.

[18] Use of pyroglutamic acid, aspartic acid, and glutamic acid in the manufacture of a liver-regenerating agent.

[19] Use of pyroglutamic acid, aspartic acid, and glutamic acid in the manufacture of a liver function-recovering agent.

[20] Use of pyroglutamic acid, aspartic acid, and glutamic acid in the manufacture of a therapeutic agent for a liver disease.

Advantageous Effects of Invention

According to the present invention, a hepatocyte-proliferating agent can be provided, which can selectively proliferate normal hepatocytes without proliferating cancer cells.

DESCRIPTION OF EMBODIMENTS

Figure 1:
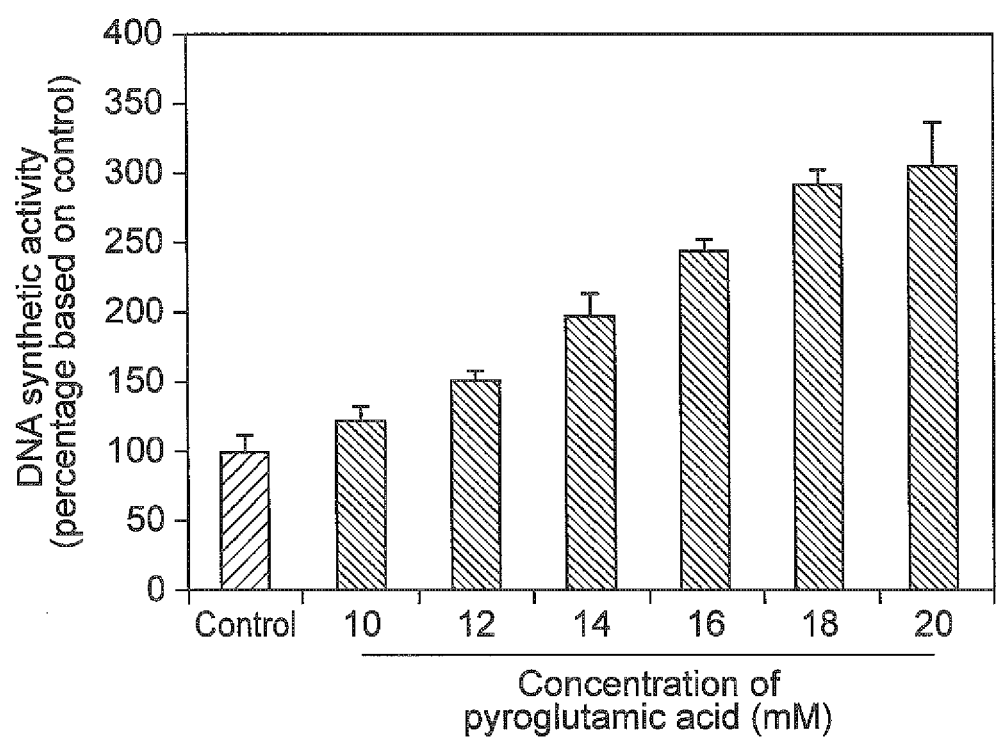
FIG. 1 is a graph showing the relative values of the activity of DNA synthesis in rat normal hepatocytes.

Preferred embodiments of the present invention will be described below in detail. However, the present invention is not intended to be limited to the following embodiments.

The hepatocyte-proliferating agent according to the present invention contains pyroglutamic acid, aspartic acid, and glutamic acid as active ingredients. Hereinafter, the hepatocyte-proliferating agent using the combination of these amino acids is called "PARI-S001".

Here, the hepatocyte-proliferating agent means an agent promoting the proliferation of normal hepatocytes in both in-vivo and in-vitro environments.

Pyroglutamic acid, aspartic acid, and glutamic acid can be used in the form of free amino acids and/or salts thereof. Pyroglutamic acid, aspartic acid, and glutamic acid may be synthesized by well-known methods from well-known compounds, or can be obtained as commercially available products. The salts of pyroglutamic acid, aspartic acid, and glutamic acid are not particularly limited provided that they are pharmacologically or physiologically acceptable salts. Specific examples of such salts include salts with inorganic bases [for example, ammonium salts; and salts with metals, such as alkaline metals (e.g., sodium and potassium), alkaline earth metals (e.g., calcium and magnesium), and alminium], and salts with organic bases [for example, salts with organic amines, such as methylamine, tritylamine, diethylamine, triethanolamine, morpholine, piperazine, pyrrolidine, tripyridine, and picoline].

The free amino acids and/or salts thereof also include those in the form of hydrates. The free amino acids and/or salts thereof may be in D-form or L-form.

For pyroglutamic acid, the above-described free amino acid and/or salts thereof may be used alone or in any combination of 2 or more. This is ditto for aspartic acid and glutamic acid. Among these, pyroglutamic acid, aspartic acid, and glutamic acid can each be preferably used in the form of a free L-form amino acid or a salt thereof in view of having an activity of proliferating hepatocytes.

When the hepatocyte-proliferating agent according to the present embodiment is a solution, the concentration of pyroglutamic acid as the main active ingredient is not particularly limited and is properly set depending on the types and concentrations of aspartic acid and glutamic acid used in combination therewith, use as a hepatocyte-proliferating agent, the form of its preparation, the method for its use, and the like.

The concentration of pyroglutamic acid in the solution is preferably 0.5 to 20 mM, more preferably 2 to 20 mM, still more preferably 10 to 20 mM, yet more preferably 12 to 20 mM, particularly more preferably 14 to 20 mM in view of effectively promoting the proliferation of hepatocytes. In addition, the concentration is preferably 0.5 to 16 mM, more preferably 12 to 16 mM, still more preferably 14 to 16 mM in view of effectively promoting the proliferation of hepatocytes while favorably maintaining the morphology (shape) of the hepatocytes.

When the hepatocyte-proliferating agent according to the present embodiment is a solution, the concentration of aspartic acid is not particularly limited and is properly set depending on the types and concentrations of pyroglutamic acid and glutamic acid used in combination therewith, use as a hepatocyte-proliferating agent, the form of its preparation, the method for its use, and the like.

The concentration of aspartic acid in the solution is preferably 0.7 to 2.8 mM, more preferably 0.7 to 1.4 mM in view of effectively promoting the proliferation of hepatocytes.

When the hepatocyte-proliferating agent according to the present embodiment is a solution, the concentration of glutamic acid is not particularly limited and is properly set depending on the types and concentrations of pyroglutamic acid and aspartic acid used in combination therewith, use as a hepatocyte-proliferating agent, the form of its preparation, the method for its use, and the like.

The concentration of glutamic acid in the solution is preferably 0.1 to 1.6 mM, more preferably 0.1 to 0.8 mM, still more preferably 0.4 to 0.8 mM in view of effectively promoting the proliferation of hepatocytes.

The molar ratio of pyroglutamic acid, aspartic acid, and glutamic acid contained in the hepatocyte-proliferating agent according to the present embodiment is not particularly limited and is properly set depending on the types of pyroglutamic acid, aspartic acid, and glutamic acid used, the use of the hepatocyte-proliferating agent, the form of its preparation, the method for its use, and the like. The molar ratio of each of the active ingredients contained in the hepatocyte-proliferating agent is preferably pyroglutamic acid:aspartic acid:glutamic acid=5 to 200:7 to 28:1 to 16, more preferably pyroglutamic acid:aspartic acid:glutamic acid=20 to 200:7 to 14:1 to 8, still more preferably pyroglutamic acid:aspartic acid:glutamic acid=100 to 200:7 to 14:4 to 8 in view of effectively promoting the proliferation of hepatocytes.

The hepatocyte-proliferating agent according to the present embodiment may consist only of pyroglutamic acid, aspartic acid, and glutamic acid as active ingredients, or comprise these active ingredients and other ingredients. Examples of the other ingredients include a stabilizer, a preservative, an additive (for example, sodium bisulfite).

The hepatocyte-proliferating agent according to the present embodiment can be used as a therapeutic agent for a liver disease, a liver-regenerating agent, or a liver function-recovering agent since it can selectively proliferate normal hepatocytes. Examples of the liver disease include liver cancer, acute hepatitis, chronic hepatitis, steatohepatitis, liver cirrhosis, fatty liver, alcoholic liver injury, non-alcoholic steatohepatitis, and liver fibrosis. The hepatocyte-proliferating agent according to the present embodiment is preferably used as a therapeutic agent for liver cancer since it does not proliferate cancer cells.

The hepatocyte-proliferating agent according to the present embodiment can be safely administered parenterally to a subject, such as a human and an animal. Examples of the parenteral administration include intravenous injection, intraarterial injection, intramuscular injection, subcutaneous injection, intradermal injection, intraperitoneal injection, transdermal administration, pulmonary administration, transnasal administration, and transmucosal administration.

Examples of the dosage form of the hepatocyte-proliferating agent according to the present embodiment include injections (e.g., a subcutaneous injection, an intradermal injection, an intravenous injection, an intramuscular injection, and an intraperitoneal injection), external preparations (e.g., a transdermal preparation and an ointment), liquids for external use (e.g., an infusion, a fomentation, and a liniment), and sustained-release preparations (e.g., sustained-release capsules).

In addition, the hepatocyte-proliferating agent according to the present embodiment can be used by being encapsulated in hydrogels or microcapsules of a bioabsorbable polymer, such as collagen, gelatin, polylactic acid, or polyglycolic acid and being injected into, or embedded in, for example, a subcutaneous, intraorgan, muscular, or peritoneal region.

Embodiments of the present invention have been described above. However, the present invention is not intended to be limited to the embodiments, and various changes can be made in the range not departing from the spirit of this invention. For example, the hepatocyte-proliferating agent may be in a form containing pyroglutamic acid and also containing aspartic acid or glutamic acid.

EXAMPLES

Materials and Experimental Methods

Reagent

The amino acids as active ingredients used were L-pyroglutamic acid (Nacalai Tesque Co., Ltd.), L-aspartic acid (Nacalai Tesque Co., Ltd.), and L-glutamic acid (Nacalai Tesque Co., Ltd.) (hereinafter, the mark of L-form is omitted). The kinase inhibitors used were Rapamycin (Sigma Co., Ltd.), PD98059 (Sigma Co., Ltd.), SB203580 (Sigma Co., Ltd.), and LY294002 (Sigma Co., Ltd.).

In what follows, PARI-S001 refers to a mixture of pyroglutamic acid (10 to 20 mM), aspartic acid (1.4 mM), and glutamic acid (0.4 mM).

Cell

Separation of Rat Normal Hepatocyte (In Situ Collagenase Perfusion Method

SD rats (6- to 7-week old, male) (purchased from Kyudo Co., Ltd.) were anesthetized by intraperitoneally administering 25% (w/v) urethane at a dose of 1.25 g/kg body weight. Then, the anesthetized SD rats were subjected to ventrotomy, and buffer A (37° C.) was perfused from the hepatic portal vein for 7 minutes, followed by further perfusing buffer B for 7 minutes. Here, buffer A is a buffer obtained by adding ethylene glycol tetraacetic acid (EGTA) to a final concentration of 0.05 M to 1 M Hepes. Buffer B is a buffer obtained by adding a solution of collagenase (Sigma Co., Ltd.) to a final concentration of 0.5 g/L to buffer A. After the perfusion was completed, the liver of the SD rats was removed, and the cells of the liver were loosened using a scalpel in a dish placed on ice to make single cells. Thereafter, DMEM medium (Dulbecco's Modified Eagle Medium) cooled with ice was added to the resultant single cells, followed by pipetting and then filtration with gauze and a 100-μm mesh to provide a cell suspension. The filtered cell suspension was transferred to a 50-ml falcon tube, and washing with DMEM medium cooled with ice and supernatant removal by centrifugation (at 50×g for 1 minute) were carried out 3 times Subsequently, the cell suspension was centrifuged at 50×g for 1 minute; the supernatant was removed; and DMEM medium cooled with ice was again added, followed by pipetting. The cells thus obtained were used for the following experiment as the normal hepatocytes of rats (rat normal hepatocytes).

Culture of Rat Normal Hepatocyte

The supernatant of the separated cell suspension was removed, and William's E medium (containing 5% fetal bovine serum (FBS), 10 nM insulin, and 10 nM dexamethasone) cooled with ice was added to dilute the cell suspension to 10 ml. A portion of the resultant cell suspension was used and subjected to trypan blue staining to measure the number of living cells. Then, the rat normal cells were seeded in a 96-well collagen-coated plate to $1.0 \times 10^4$ cells/well and cultured at 37° C.

Cancer Cell Line

The liver cancer cells used were the following cell lines. HepG2 (National Institute of Biomedical Innovation, JCRB Cell Bank; hereinafter abbreviated as "JCRB") and FILE (JCRB) were each cultured in 10% serum-containing DMEM medium. Huh-7 (JCRB) was cultured in 10% serum-containing RPMI medium.

Normal Cell Proliferation Test

The rat normal cells ($1.0 \times 10^4$ cells/well) were cultured for 3 hours after seeding in the 96-well plate, followed by replacement with the medium to which each PARI-S001 was added. The cells cultured for 22 hours thereafter were tested for cell proliferation using a Cell Proliferation ELISA BrdU (colorimetric) Kit (Roche Co., Ltd.).

Cancer Cell Proliferation Test

HepG2 ($2.5 \times 10^3$ cells/well), HLE ($2.5 \times 10^3$ cells/well), and Huh-7 ($1.0 \times 10^3$ cells/well) were each cultured for 24 hours after seeding in the 96-well plate, followed by replacement with the medium to which each PARI-S001 was added. The cells cultured for 24, 48, or 72 hours thereafter were quantified for the protein amount in each well by an SRB assay method to be described later. Then, the activity of cell proliferation was evaluated based on the quantitated protein amount.

SRB Assay Method

The SRB assay method is used for the measurement of cell density based on the measurement of the cell protein content. The specific procedure was carried out as follows.

The cells were seeded in a 96-well plate, and each PAM-S001 was added thereto. 25 μL/well of a 50% trichloroacetic acid (hereinafter, sometimes referred to as "TCA") solution was added thereto 24 hours, 48 hours, or 72 hours after adding PARI-S001, and incubation was carried out in a refrigerator at 4° C. for 1 hour. 1 Hour later, the solution was removed, and each well was washed 4 times with 300 μL/well of Milli Q water to remove TCA. Thereafter, the 96-well plate was turned upside down and lightly tapped to remove the excess water. In addition, the 96-well plate was allowed to stand for 1 hour or more for air-drying. 50 μL/well of a sulforhodamine B solution was added to the dried well, which was then allowed to stand at room temperature. The sulforhodamine B solution was removed 20 to 30 minutes thereafter, and each well was washed 4 times with 300 μL/well of a 1% acetic acid solution. The plate was turned upside down and lightly tapped to remove the excess water. Further, the 96-well plate was allowed to stand for 1 hour or more for air-drying. After air-drying the plate, 100 μL/well of a lysis solution (10 mM Tris Base solution (pH 7.4)) was added thereto. Then, the 96-well plate was stirred for 2 minutes in a shaker to lyse the cells, and absorbance at 565 nm was measured using a multiwell spectrophotometer (μQuant).

Intracellular Signaling Pathway Analysis Using Inhibitor

The intracellular signaling pathway analysis was carried out in order to clarify through which intracellular signaling pathway the PARI-S001 promoted cell proliferation activity. PARI-S001 and various kinase inhibitors were used to measure the cell proliferation activity. The measurement method used was the same method as that in the above-described <Normal Cell Proliferation Test>.

Results

DNA Synthesis Activity with PARI-S001 (Pyroglutamic Acid Concentration: 10 to 20 mM)

FIG. 1 shows the results of measuring DNA synthesis activity in the primary liver cells of the normal rats (normal rat primary liver cells) when PARI-S001 whose pyroglutamic acid concentration was varied in the range of 10 mM to 20 mM was added. A higher DNA synthesis activity can be evaluated to result in a higher proliferation rate of normal rat primary liver cells. The control used was DNA synthesis activity in the rat normal primary liver cells to which nothing was added. The ordinate in FIG. 1 represents the relative values (percent) of DNA synthesis activity based on the control.

As shown in FIG. 1, the DNA synthesis activity in normal rat primary liver cells increased depending on the concentration of pyroglutamic acid contained in PARI-S001. When the concentration of pyroglutamic acid was 10 mM to 14 mM, the morphology of normal rat primary liver cells was the same as the morphology of control cells.

Cell Proliferation Assay of Liver Cancer Cell Line Using PARI-S001

Figure 2:
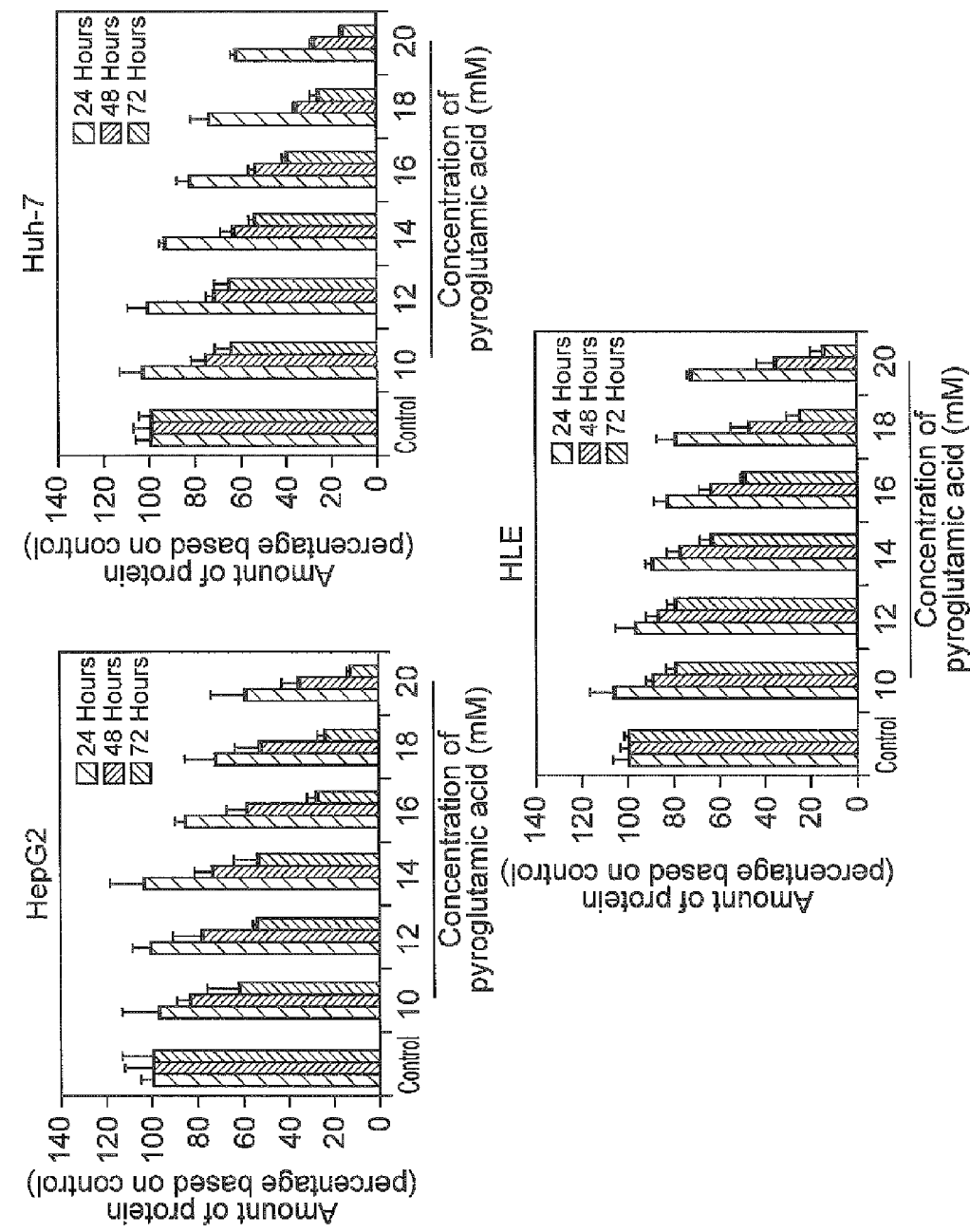
FIG. 2 is a graph showing the relative values of the amounts of protein contained in liver cancer cell lines.

FIG. 2 shows the results of measuring the content of protein in liver cancer cell lines (HepG2, HLE, and Huh-7) when PARI-S001 whose pyroglutamic acid concentration was varied in the range of 10 mM to 20 mM was added. The higher content of protein (amount of protein) can be evaluated to result in the higher proliferation rate of the liver cancer cell lines. In contrast, the lower content of protein can be evaluated to result in inhibiting the proliferation of the liver cancer cell lines. The protein amount was quantified by the above-described SRB assay method. The control used was the protein content in liver cancer cells to which nothing was added. The SRB assay method was carried out after a lapse of 24 hours, 48 hours, or 72 hours after adding PARI-S001 to the cells. The ordinate in FIG. 2 represents the relative values (percent) of the protein content based on the control.

As shown in FIG. 2, the protein content in the liver cancer cell lines decreased compared to the control at 48 hours and later after adding PARI-S001 to the cells. This showed that the proliferation of the liver cancer cell lines was suppressed depending on the concentration of pyroglutamic acid contained in PARI-S001 and further as the culture time elapsed in the presence of PARI-S001. These results showed that the hepatocyte-proliferating agent containing pyroglutamic acid, aspartic acid, and glutamic acid as active ingredients was also useful as a therapeutic agent for liver diseases, such as liver cancer.

Analysis of Intracellular Signaling Pathway Using Inhibitor

The rat normal hepatocytes were cultured for 3 hours after seeding, followed by replacement with the medium to which PAM-S001 (pyroglutamic acid concentration: 10 mM) and each kinase inhibitor were simultaneously added. The concentration of rapamycin (an inhibitor of mTOR) was adjusted to a final concentration of 1.6 ng/mL, 3.1 ng/mL, 6.3 ng/mL, or 12.5 ng/mL. The concentration of PD98059 (an inhibitor of MEK1 and MEK2), SB203580 (an inhibitor of p38 of MAPK), and LY294002 (an inhibitor of PI3K) was adjusted to a final concentration of 6.3 μM, 12.5 μM, 25 μM, or 50 µM. To promote the dissolution of each kinase inhibitor, dimethyl sulfoxide (hereinafter abbreviated as "DMSO") was added to a final concentration of 0.5% to the medium. Similarly, DMSO was added to a final concentration of 0.5% to the control. Culture was further carried out for 22 hours after medium replacement, followed by evaluating DNA synthesis activity using a Cell Proliferation ELISA BrdU (colorimetric) Kit (Roche Co., Ltd.).

The simultaneous addition of PARI-S001 (pyroglutamic acid concentration: 10 mM) and PD98059 was found to suppress DNA synthesis activity in the rat normal hepatocytes depending on the concentration of the inhibitor. In contrast, the simultaneous use of PARI-S001 (pyroglutamic acid concentration: 10 mM) and each of the other inhibitors was not observed to change the DNA synthesis activity even when the inhibitor concentration was increased. This demonstrated that PARI-S001 induced cell proliferation through the intracellular signaling pathway via MEK1 and MEK2.

The invention claimed is:

1. A method for proliferating normal hepatocytes, comprising a step of adding effective amounts of pyroglutamic acid, aspartic acid, and glutamic acid to the normal hepatocytes in vitro,
wherein a molar ratio of each of active ingredients is pyroglutamic acid:aspartic acid:glutamic acid=5 to 200:7 to 28:1 to 16.

2. The method according to claim 1, wherein pyroglutamic acid, aspartic acid, and glutamic acid form a solution, in which a concentration of pyroglutamic acid is 0.5 to 20 mM.

3. The method according to claim 1, wherein pyroglutamic acid, aspartic acid, and glutamic acid form a solution, in which a concentration of aspartic acid is 0.7 to 2.8 mM and a concentration of glutamic acid is 0.1 to 1.6 mM.

4. A method for regenerating a liver or recovering liver function, comprising a step of administering effective amounts of pyroglutamic acid, aspartic acid, and glutamic acid to a subject in need thereof,
wherein a molar ratio of each of active ingredients is pyroglutamic acid:aspartic acid:glutamic acid=5 to 200:7 to 28:1 to 16.

5. The method according to claim 4, wherein pyroglutamic acid, aspartic acid, and glutamic acid form a solution, in which a concentration of pyroglutamic acid is 0.5 to 20 mM.

6. The method according to claim 4, wherein pyroglutamic acid, aspartic acid, and glutamic acid form a solution, in which a concentration of aspartic acid is 0.7 to 2.8 mM and a concentration of glutamic acid is 0.1 to 1.6 mM.

7. The method according to claim 4, wherein the subject is a human.

8. A method for treating a liver disease, comprising a step of administering effective amounts of pyroglutamic acid, aspartic acid, and glutamic acid to a subject suffering from the liver disease,
wherein the liver disease is selected from the group consisting of liver cancer, acute hepatitis, chronic hepatitis, steatohepatitis, liver cirrhosis, fatty liver, alcoholic liver injury, non-alcoholic steatohepatitis, and liver fibrosis,
wherein a molar ratio of each of active ingredients is pyroglutamic acid:aspartic acid:glutamic acid=5 to 200:7 to 28:1 to 16.

9. The method according to claim 8, wherein pyroglutamic acid, aspartic acid, and glutamic acid form a solution, in which a concentration of pyroglutamic acid is 0.5 to 20 mM.

10. The method according to claim 8, wherein pyroglutamic acid, aspartic acid, and glutamic acid form a solution, in which a concentration of aspartic acid is 0.7 to 2.8 mM and a concentration of glutamic acid is 0.1 to 1.6 mM.

11. The method according to claim 8, wherein the subject is a human.

12. The method according to claim 8, wherein the liver disease is liver cancer.

* * * * *